United States Patent [19]

Winkel et al.

[11] Patent Number: 4,628,112
[45] Date of Patent: Dec. 9, 1986

[54] AMINES, PROCESSES FOR THEIR PREPARATION AND THEIR USE IN COMPOSITIONS WHICH CAN UNDERGO FREE RADICAL POLYMERIZATION

[75] Inventors: Jens Winkel, Cologne; Gerhard Klein, Monheim; Helmut-Martin Meier, Hattingen; Carlhans Süling, Odenthal; Dieter Arlt, Cologne, all of Fed. Rep. of Germany

[73] Assignee: Bayer Aktiengesellschaft, Leverkusen, Fed. Rep. of Germany

[21] Appl. No.: 675,689

[22] Filed: Nov. 28, 1984

[30] Foreign Application Priority Data

Dec. 13, 1983 [DE] Fed. Rep. of Germany ....... 3345103

[51] Int. Cl.⁴ ......................................... C07C 125/065
[52] U.S. Cl. ...................................... 560/160; 106/35; 526/204; 526/213; 544/169; 546/233; 548/567; 560/221
[58] Field of Search ................ 560/160, 221; 544/169; 546/233; 548/567

[56] References Cited

U.S. PATENT DOCUMENTS 4,243,763 1/1981 Argentar ............................... 525/27

FOREIGN PATENT DOCUMENTS 331518 8/1976 Austria .
42991 1/1982 European Pat. Off. .
2336264 2/1975 Fed. Rep. of Germany .

*Primary Examiner*—Michael L. Shippen
*Attorney, Agent, or Firm*—Sprung, Horn, Kramer & Woods

[57] ABSTRACT

Compounds of the formula

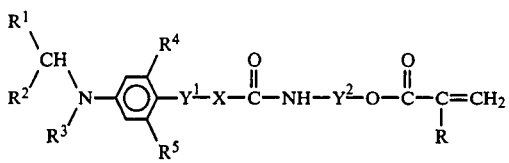

in which

R represents hydrogen or a methyl group, $Y^1$ represents an optionally branched alkylene radical with 1 to 6 C atoms, $Y^2$ represents an optionally branched alkylene radical with 2 to 8 C atoms, X denotes oxygen or an —NH— group, $R^1$ and $R^2$ are identical or different and denote hydrogen, or an alkyl, alkenyl, cycloalkyl, cycloalkenyl, aryl, aralkyl or alkylaryl group which has 1 to 11 C atoms and is optionally substituted by one or more, hydroxyl, amino, epoxide, urethane, urea, ester or ether groups, or $R^1$ and $R^2$ together form a 3-membered to 6-membered ring, which optionally contains nitrogen, oxygen or sulphur as hetero-atoms, $R^3$ has the meaning of $R^1$ or represents a group

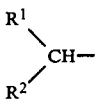

or $R^2$ and $R^3$, together with the

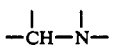

group, form a 5-membered or 6-membered ring, which optionally contains oxygen as a further heteroatom, and $R^4$ and $R^5$ are identical or different and represent hydrogen, an alkyl or alkenyl group which has 1 to 10 C atoms and is optionally substituted by halogen, or halogen, function as activators in the free radical polymerization of olefinically unsaturated monomers.

12 Claims, No Drawings

AMINES, PROCESSES FOR THEIR PREPARATION AND THEIR USE IN COMPOSITIONS WHICH CAN UNDERGO FREE RADICAL POLYMERIZATION

The invention relates to new tertiary aromatic amines which contain unsaturated groups, processes for their preparation and compositions, in particular dental compositions, which can undergo free radical polymerization and contain these amines as activators.

The polymerization of ethylenically unsaturated compounds, such as styrene, acrylic acid, methacrylic acid or monofunctional or polyfunctional acrylates or methacrylates, is initiated by free radicals. These free radicals can be formed, inter alia, by organic peroxides. If diacyl peroxides are used as free radical initiators, the dissociation of the peroxides can be accelerated to a considerable degree by tertiary aromatic amines.

Systems of this type are used, for example, for the preparation of polymers based on polyfunctional acrylates or methacrylates, which are used, inter alia, in the dental field as tooth fillings or tooth replacements or as bone cements. However, after the polymerization reaction, the polymers thus prepared still contain free amine which is not chemically bonded to the high molecular weight chains, and also reaction products of the amine with the diacyl peroxide.

The possibility of diffusion of the substances into the surrounding medium can be a serious hindrance to the use of the polymers in the field of medicine.

There has therefore been no lack of attempts to synthesize amines which have groups which can be copolymerized with the ethylenically unsaturated compounds in order thus to bond the amines, or reaction products thereof, chemically to the polymer. A route which is obvious per se consists in preparing (meth)acrylates of tertiary aminoalcohols The copolymerizable (meth)acrylates of tertiary amines containing OH groups which have as yet been disclosed, however, all have a considerably lower activity in respect of acceleration of the peroxide dissociation than the free amines (Fr. Hrb/ák, V. Hynkov/á; Makromol. Chem. 176, 1669–1678 (1975)).

Surprisingly, it has now been found that the tertiary amines, described below, containing urethane groups or urea groups have at least an equivalent activity, and as a rule even a higher activity, than the corresponding aminoalcohols.

The invention relates to tertiary aromatic amines of the general formula (I):

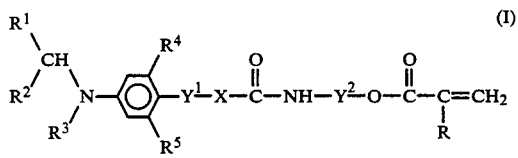

in which

R represents hydrogen or a methyl group, $Y^1$ represents an optionally branched alkylene radical with 1 to 6 C atoms, preferably 1 to 3 C atoms, $Y^2$ represents an optionally branched alkylene radical with 2 to 8 C atoms, preferably 2 to 5 C atoms, X denotes oxygen or an —NH— group, $R^1$ and $R^2$ are identical or different and denote hydrogen, or an alkyl, alkenyl, cycloalkyl, cycloalkenyl, aryl, aralkyl or alkylaryl group which has 1 to 11 C atoms and is optionally substituted by one or more, preferably only one, hydroxyl, amino, epoxide, urethane, urea, ester or ether group, or $R^1$ and $R^2$ together form a 3-membered to 6-membered ring, which optionally contains nitrogen, oxygen or sulphur as hetero-atoms, $R^3$ has the meaning of $R^1$ or represents a group

or $R^2$ and $R^3$, together with the

group, form a 5-membered or 6-membered ring, which optionally contains oxygen as a further heteroatom, and $R^4$ and $R^5$ are identical or different and represent hydrogen, an alkyl or alkenyl group which has 1 to 10 C atoms and is optionally substituted by halogen, or halogen.

Compounds which are preferred according to the invention are those in which $R^1$ represents hydrogen. Furthermore, $R^2$ preferably represents hydrogen or methyl (in particular hydrogen); $R^3$ is preferably methyl or ethyl, in particular methyl. $R^4$ and $R^5$ preferably represent hydrogen or methyl.

The invention also relates to a process for the preparation of compounds of the general formula (I), which is characterized in that tertiary amines of the general formula (II)

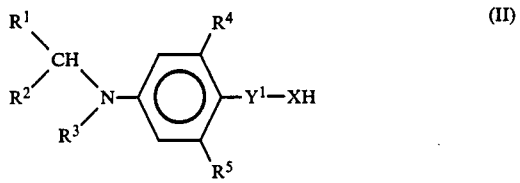

are reacted with isocyanates of the general formula (III)

wherein R, $R^1$ to $R^5$, $Y^1$, $Y^2$ and X have the abovementioned meaning,
at temperatures as a rule between −30° C. and 150° C., preferably between 0° and 50° C., if appropriate in an inert organic solvent.

The invention furthermore relates to the use of compounds of the formula (I) as activators in compositions which undergo free radical polymerization.

The invention also relates to polymerizable compositions containing an olefinically unsaturated monomer, a tertiary aromatic amine and, if appropriate, organic and/or inorganic fillers and/or other auxiliaries and additives which are known per se, the amine being a compound of the formula (I).

The amines of the formula (II) and isocyanates of the formula (III) used for the preparation of the compounds according to the invention are known, or they can be obtained by known processes:

The amines of the formula (II) can be obtained by methods which are known from the literature, such as those described, for example, in G. Ferri, Reaktionen der organischen Synthese (Reactions of Organic Synthesis), Georg Thieme Verlag, Stuttgart (1978) Chapter 1.3 or in Chapter 8.

Isocyanates of the formula (III) can be obtained by a process in which dihydrooxazines, optionally in the form of acid adducts, are reacted with phosgene at $-20°$ to $+20°$ C. in a water-immiscible solvent in the presence of an aqueous solution of a base, the dihydrooxazines having the general formula

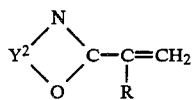 (IV)

The dihydrooxazines (IV) to be used as starting materials are prepared by processes analogous to those of the prior art. Thus, the starting compounds (IV) can be prepared, for example, from N-hydroxy-methylamides of the general formula

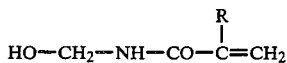 (V)

and an olefin by the process described in Liebig's Annalen 697, pages 171–180 (1966).

They are more advantageously obtained from formaldehyde, a nitrile of the general formula

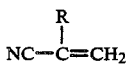 (VI)

and an olefin by a process analogous to that described in Synthesis (1971), pages 92–95.

In this process, formaldehyde is reacted with the nitrile of the general formula (VI) is a solvent in the presence of equimolar amounts of a strong acid in a temperature range between 30° and 100° C., preferably at 50°–60° C.

The amidomethylium ion thereby formed, of the formula

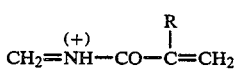 (VII)

reacts with the olefin in a polar cycloaddition reaction to give the acid adduct of the dihydrooxazine, from which the dihydrooxazine (IV) suitable as the starting material can be obtained by treatment, which is known per se, with a base.

The formaldehyde here can be obtained either by depolymerization from paraformaldehyde or from 1,3,5-trioxane. Solvents which can be used are carboxylic acids, carboxylic acid anhydrides, ethers, such as, for example, tetrahydrofuran, dioxane, glyme and diglyme, amides, such as, for example, N-methylpyrrolidone, urea, such as, for example, 1,3-dimethylpyrrolid-2-one, or sulpholane. Carboxylic acids, in particular acetic acid, are preferred.

Possible strong acids are sulphuric acid, phosphoric acid, hydrogen chloride, hydrogen fluoride, hydrofluoboric acid and sulphonic acids. Sulphuric acid is most advantageously used. Exclusion of water is to be ensured in all cases.

The nitrile is added, in equimolar amounts in a temperature range of between 30° and 100° C., preferably at 50°–60° C, to a solution of formaldehyde and the strong acid in the solvent. Cis-but-2-ene, trans-but-2-ene and but-1-ene, if appropriate as a mixture, for example, are suitable as the olefin or olefin mixture. Such technical grade butene mixtures, which, besides reactive butenes, also contain inert butanes, are obtained, for example, as the $C_4$ fraction in distillative separation of the cracking products from naphtha crackers. Other large-scale industrial $C_4$ fractions from naphtha crackers with a high content of iso-butene enable dihydrooxazine mixtures with a high content of 6,6-dimethyl-substituted isomers to be prepared. Since the 1-butene contained in the fractions mentioned is slower to react than cis- and trans-but-2-ene, the content of 6-ethyl-2-vinyl-5,6-dihydrooxazine in the dihydrooxazine mixtures is generally smaller than the content of but-1'-ene in the $C_4$ fraction employed.

The reaction between the acid adduct of the dihydrooxazine and the olefin or olefin mixture can be carried out in an open vessel with the olefin being passed through or added dropwise, and, in the case of gaseous olefins, also under pressure.

The dihydrooxazine is formed from the amidomethylium ion (VII) and the olefin in a stereospecific cis-addition reaction (see Chem. Ber. 103, 3242 (1970). A corresponding cis/trans mixture of the 5,6-dimethyl-dihydrooxazine is therefore formed from a cis/trans-olefin mixture.

As already mentioned, the free dihydrooxazine can be liberated from the resulting acid adduct in a manner which is known per se by means of a base, such as, for example, sodium hydroxide or potassium hydroxide. However, it is also possible to use the dihydrooxazines in the form of their acid adducts.

The dihydrooxazines or dihydrooxazine mixtures are preferably phosgenated by the known two-phase phosgenation process, such as is described, for example, in DE-AS (German Published Specification) No. 1,924,535 for the phosgenation of oxazolines or of dihydrooxazines. In general, 1 to 2 moles of phosgene are used per mole of dihydrooxazine or per mole of acid adduct of the dihydrooxazine, and at least 2 moles of an aqueous base are employed per mole of phosgene. If acid adducts of the dihydrooxazines are used, an amount of base equivalent to the acid is also additionally required.

Aqueous solution of alkali metal hydroxides and carbonates can be used as the bases. Aqueous sodium hydroxide solution is preferred. The dihydrooxazine and phosgene are in general used as solutions in a non-polar, water-immiscible solvent. Hydrocarbons, halogenohydrocarbons, such as, for example, methylene chloride, chloroform, 1,2-dichloropropane, chlorobenzene and dichlorobenzene, esters, such as, for example, ethyl acetate, or ethers, such as diethyl ether or dibutyl ether, are suitable here. It is most advantageous to use halogenohydrocarbons, in particular methylene chloride.

The solutions of the dihydrooxazine, the phosgene and the base are introduced simultaneously and uniformly into the reaction vessel. Intensive thorough mixing is to be ensured here. The temperature is kept at −20° to +20° C., preferably between 0° and 5° C. Since the reaction proceeds very rapidly, a continuous procedure is advantageous.

Other synthesis methods for the isocyanates of the formula (III) are described, for example, in U.S. Pat. No. 2,718,516 and U.S. Pat. No. 2,821,544.

The monomers to be used in the compositions according to the invention contain at least one double bond which can undergo free radical polymerization. Monomers with more than one double bond and boiling points above 100° C. under 13 mbar are preferably used, by themselves or optionally as a mixture with monofunctional monomers. Highly crosslinked polymers or copolymers are thereby obtained. The molecular weights of the monomers can be between about 70 and 20,000, preferably between about 150 and 1,000. The viscosity of the monomers can be adjusted by suitable admixing of monomers of higher viscosity or higer molecular weight with monomers of low viscosity. The monomers optionally contain small amounts polymerization inhibitors, such as, for example, 0.01–0.2% of 2,6-di-t-butyl-p-cresol.

Examples of possible monomers which can be polymerized according to the invention are: esters of unsaturated mono- or di-carboxylic acids, for example esters of acrylic acid, methacrylic acid α-cyanoacrylic acid, crotonic acid, cinnamic acid, sorbic acid, maleic acid, fumaric acid or itaconic acid, with aliphatic, cycloaliphatic or aromatic-aliphatic mono-, di-, tri- or tetrahydric alcohols with 2–30 carbon atoms, for example methyl (meth)acrylate, n-, i- and t-butyl (meth)acrylate, 2-ethylhexyl acrylate, lauryl acrylate, dihydrodicyclopentadienyl (meth)acrylate, dihydroxmethyl-tricyclo[5,2,1,0$^{2,6}$]decane di(meth)acrylate according to German Patent Specification No. 2,200,021, ethylene glycol diemthacrylate, hydroxyethyl (meth)acrylate, hydroxypropyl (meth)acrylate, ethylene glycol diacrylate, diethylene glycol diacrylate, triethylene glycol di(meth)acrylate, neopentyl glycol di(meth)acrylate, 1,4-dimethylolcyclohexane diacrylate, pentaerythritol tri- and tetra-(meth)acrylate, trimethylolpropane tri(meth)acrylate, ethyl α-cyanoacrylate, ethyl crotonate, ethyl sorbate, diethyl maleate, diethyl fumarate and the di(meth)acrylate of oxyalkylated bisphenol A according to U.S. Pat. Nos. 3,810,938 and 3,923,740, di(meth)acrylates of oxyalkylated trimethylolpropane or pentaerythritol according to U.S. Pat. No. 3,380,831 and also the (meth)acrylic esters of oxyalkylated di-(hydroxymethyl)-tricyclo[5,2,1,0$^{2,6}$]decanes, such as are described in DE-OS (German Published Specification) No. 2,931,925 and DE-DS No. 2,931,926.

Other monomers which can be used in the compositions according to the invention are amides of (meth)acrylic acid, which can optionally be substituted by alkyl, alkoxyalkyl or hydroxyalkyl radicals on the nitrogen atom, such as, for example, N-isobutylacrylamide, diacetoneacrylamide, N-methylolacrylamide, N-methoxymethylacrylamide, N-butoxymethylmethacrylamide, ethylene glycol bis-(N-methylolacrylamide) ether and methylene-bis-acrylamide; triacrylformal; vinyl esters of mono- and di-carboxylic acids with 2 to 20 carbon atoms, for example vinyl acetate, vinyl propionate, vinyl 2-ethylhexanoate, vinyl versatate and divinyl adipate; vinyl ethers of monohydric or dihydric alcohols with 3 to 20 carbon atoms, for example isobutyl vinyl ether, octadecyl vinyl ether, ethylene glycol divinyl ether and diethylene gylcol divinyl ether; mono-N-vinyl compounds, for example N-vinylprrolidone, N-vinylpiperidone, N-vinylcaprolactam, N-vinylmorpholine, N-vinyloxazolidone, N-vinylsuccinimide, N-methyl-N-vinyl-formamide and N-vinylcarbazole; allyl ethers and esters, for example trimethylolpropane diallyl ether, trimethylolpropane triallyl ether, allyl (meth)acrylate, diallyl maleate, diallyl phthalate and prepolymers thereof, and any desired mixtures of all the unsaturated compounds listed.

The epoxide acrylates and urethane acrylates are particularly suitable for medical purposes. Examples of such compounds which may be mentioned are:

(a) reaction products of monofunctional epoxides and (meth)acrylic acids according to U.S. Pat. No. 2,484,487 and U.S. Pat. No. 2,575,440;

(b) reaction products of bifunctional epoxides and unsaturated fatty acids according to U.S. Pat. No. 2,456,408;

(c) reaction products of polyfunctional aromatic or aliphatic glycidyl ethers and (meth)acrylic acid according to U.S. Pat. Nos. 3,179,623, 3,066,112 and 2,824,851 and German Patent Specification No. 1,644,817;

(d) reaction products of epoxide resins and (meth)acrylyl chloride according to U.S. Pat. No. 3,427,161 and U.S. Pat. No. 2,890,202;

(e) unsaturated polyurethanes (urethane acrylates) and polyureas from hydroxyalkyl (meth)acrylates, aminoalkyl (meth)acrylates and, if appropriate, polyols or polyamines, such as are described in U.S. Pat. Nos. 3,425,988, 3,709,866, 3,629,187, 4,089,763 and 4,110,184 and in German Patent Specification Nos. 1,644,798, 1,644,797, DOS (German Published Specification) Nos. 2,357,402, 2,357,324 and 2,358,948.

Further examples of suitable comonomers can be seen from the list below; in the structural formulae, R represents

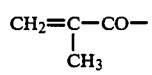

or CH$_2$=CH—CO—

R' represents H or CH$_2$—OR, n represents a number between 1 and 4 and m represents a number between 0 and 4.

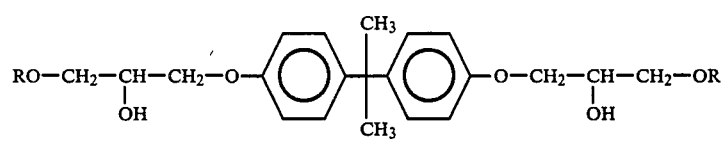

-continued
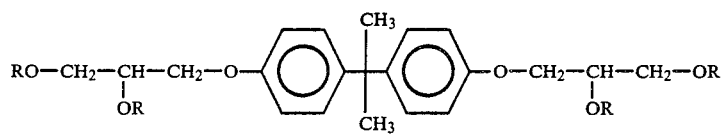
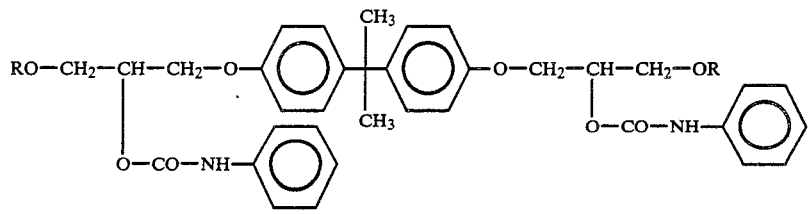
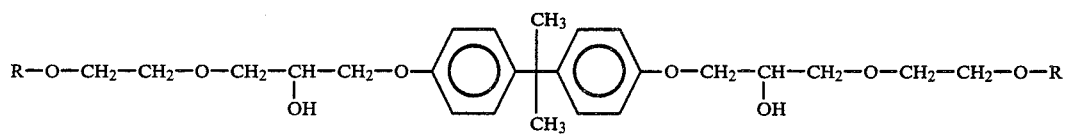
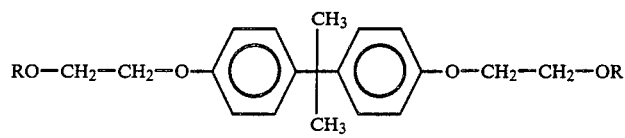
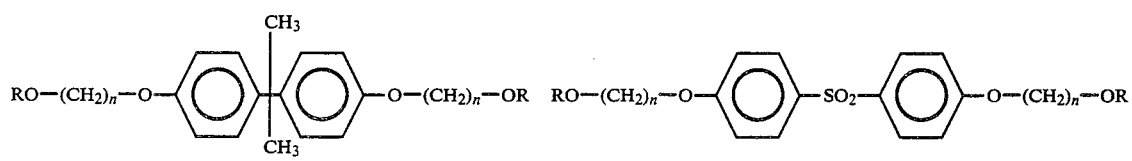
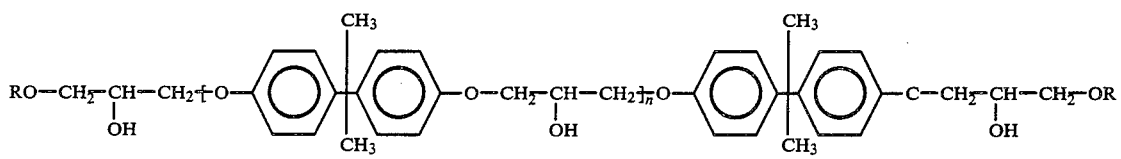
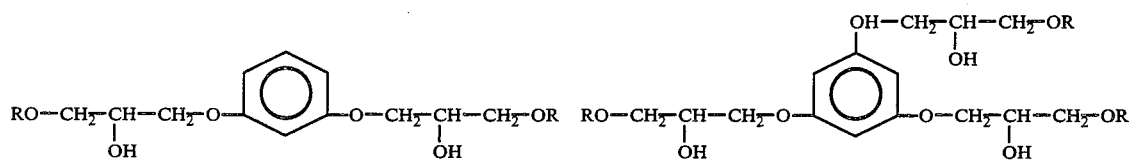
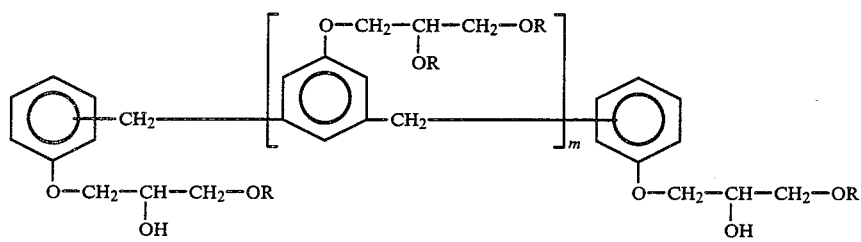
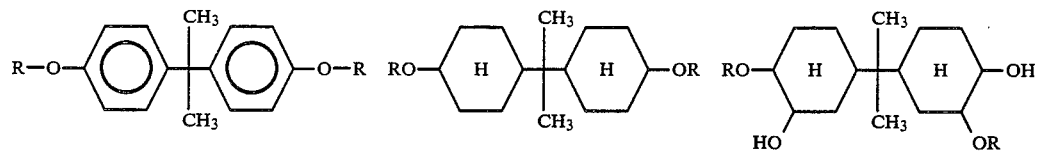

-continued
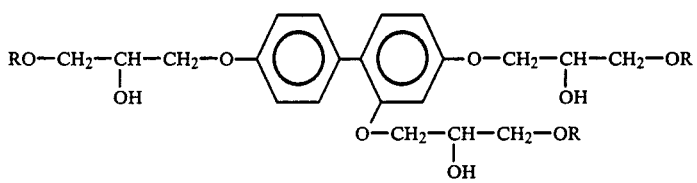
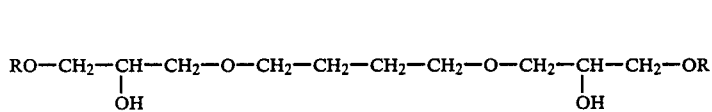
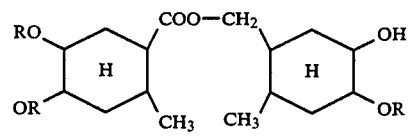
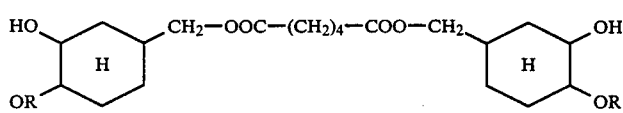
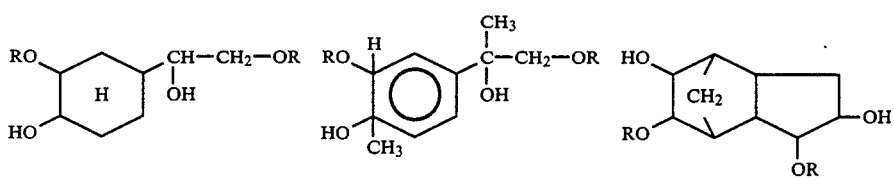
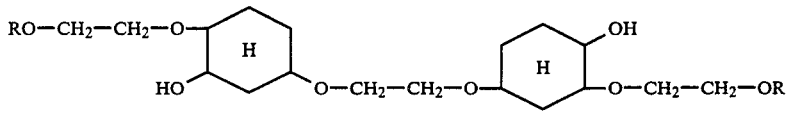
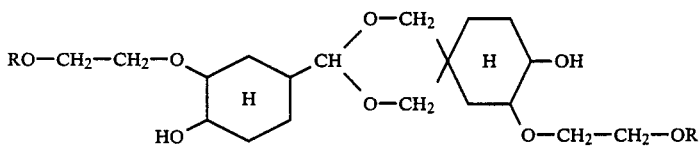
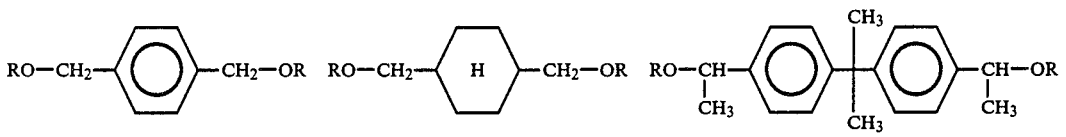
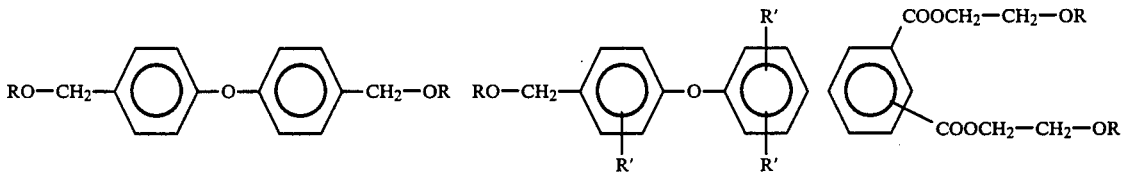
in the ortho-, meta- or para-form
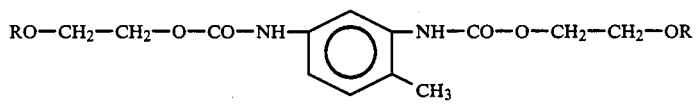

-continued

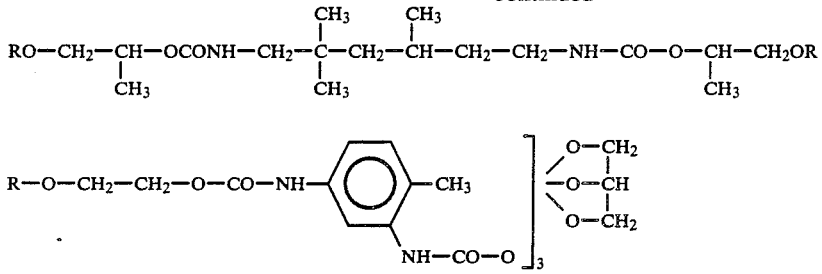

and compounds of the general formula

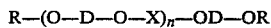

wherein
HO—D—OH represents a polyol and
HO—X—OH represents a dicarboxylic acid, each of which can be saturated or unsaturated and cyclic or acyclic.

Depending on the intended use, other substances can also additionally be used in the compositions according to the invention, such as, for example, inorganic and/or organic fillers and pigments, stabilizers, dyestuffs, particular light stabilizers, fluorescence agents, plasticizers and soluble, swellable or insoluble high molecular weight compounds.

The particle size of fillers can be, for example, between 10 nm and about 50 μm. Examples of possible inorganic fillers are metal oxides, silicates, phosphates, sulphates, carbonates and fluorides. Specific examples which may be mentioned are: rock crystal, quartzite, novaculite, cristobalite, quartz glass, highly disperse silicic acid, aluminum oxide, zirconium dioxide, titanium dioxide, barium sulphate, calcium fluoride, barium silicates or calcium silicates, β-eucryptite, spodumen, borosilicate glasses, glass ceramics, for example based on μ-cordierite, and glass ceramics containing lanthanum and zirconium, in accordance with DE-OS (German Published Specification) No. 2,347,591.

The inorganic fillers are preferably pretreated with an adhesion promoter in order to increase the bonding to the polymer matrix. Silanes, such as trimethoxy-(3-methacrylyloxypropyl)-silane, or titanic acid esters are particularly suitable for this.

Examples of organic fine-particled fillers which are used are polymers which have been prepared by polymerization of vinyl monomers, graft polymerization, polyaddition or polycondensation. Vinyl polymers which have been prepared by bulk, suspension, emulsion or precipitation polymerization are generally used. The degree of swelling of the polymer can be reduced by copolymerization of polyfunctional monomers.

Examples of suitable polymers which may be mentioned are homopolymers and copolymers of (meth)acrylates, such as methyl methacrylate, ethyl acrylate, butyl methacrylate, dodecyl methacrylate, ethylene glycol dimethacrylate, triethylene glycol dimethacrylate, bisphenol diglycidyl dimethacrylate and 1,12-dodecanediol dimethacrylate. Polymers which have been obtained according to DE-OS (German Published Specification) No. 2,849,280 are also particularly suitable.

The organic fine-particled fillers can also contain inorganic microfine substances in finely divided form. Hybrid fillers can be obtained as polymer chips by bulk polymerization of mixtures of monomer and microfine inorganic substances and then comminution of the product by grinding. Such hybrid fillers can be prepared in bead form in accordance with DE-OS (German Published Specification) No. 2,849,936.

Agents which form free radicals and can be used for the compositions according to the invention are all the organic peroxides which are known per se.

Examples of preferred initiators are diacetyl peroxide, dibenzoyl peroxide, bis(4-chlorobenzoyl)peroxide, bis(2-methylbenzoyl)peroxide, phthaloyl peroxide, succinyl peroxide, dilauroyl peroxide, acetylcyclohexanesulphonyl peroxide, isopropyl percarbonate, cyclohexyl percarbonate and bis-(4-tert.-butylcyclohexyl) percarbonate. Other suitable initiators are peroxyesters, such as tert.-butyl peroxyacetate, tert.-butyl peroxybenzoate, tert.-butyl peroctoate, dicyclohexyl peroxydicarbonate and 2,5-dimethylhexane 2,5-diperoctoate, alkyl peroxides, such as bis-(tert.-butylperoxybutane), dicumyl peroxide and tert.-butylcumyl peroxide, hydroperoxides, such as cumene hydroperoxide, tert.-butyl hydroperoxide, cyclohexanone hydroperoxide and methyl ethyl ketone hydroperoxide, perketals or ketone peroxides, such as acetylacetone peroxide.

The compounds according to the invention are preferably added in a concentration of 0.1–5% by weight, based on the total amount of olefinically unsaturated monomers, to the reaction mixture to be polymerized. 0.2–2% by weight is particularly preferably used.

The organic peroxide which serves as an agent which forms free radicals should be present, as is customary, in a concentration of 0.2 to 4% by weight, preferably 0.5 to 2% by weight, based on the monomers.

The compounds according to the invention can in principle be used in a mixture with any other component (except for the peroxide) of the polymerizable composition. However, a procedure is preferably followed (especially in the presence of fillers in the polymerizable composition) according to the teaching of U.S. Pat. No. 3,926,906, in which the tertiary amine is mixed with about half of the polymerizable monomer and about half of the filler, which is also used if appropriate, to give an "activator paste", while a "catalyst paste" is prepared from the peroxide and the remainder of the monomer and filler. The activator and catalyst pastes are then mixed in a ratio of about 1:1 immediately before use, after which the composition hardens by polymerization within a short time.

As rule, the activator paste contains, in addition to the monomer or monomers, up to 90% by weight, preferably 50 to 85% by weight, based on the total paste, of one of the abovementioned organic and/or inorganic fillers, 0.1 to 20% by weight, based on the monomer(s), of the tertiary amine and, if appropriate, up to 5% by weight, based on the total paste, of auxiliaries and additives (for example light stabilizers, antioxidants or dyestuffs).

Since the polymerizable activators of the formula (I) are incorporated into the polymer matrix, they are particularly suitable for the preparation of polymers which come into contact with the human body, for example bone cements, dental cements, dental filling compositions and medicinal sealing compositions. Moreover, as a result of their low basicity, they also do not irritate tissue.

EXAMPLE 1

(A)

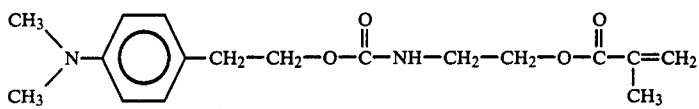

1.5 g of 4-hydroxyethyl-N,N-dimethylaniline are reacted with 1.4 g of isocyanatoethylmethacrylate in chloroform. After the solvent has been distilled off, 3.8 g of a white solid are obtained, which can be further purified by chromatography on silica gel with toluene-/ethyl acetate (7:3).

Melting point: 72° to 74° C.

$^1$H-NMR: δ=1.92(3H), 2.62-2.92(2H); 2.92(6H); 3.35-3.68(2H); 3.98-4.38(4H); 4.90(1H); 5.52-6.15(2H) and 6.62-7.18(4H).

The following compounds are obtained in an analogous manner from the corresponding alcohols or amines and isocyanato(meth)acrylates:

(B)

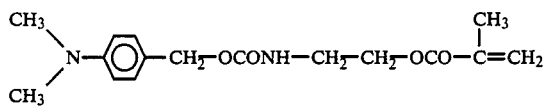

$^1$H-NMR: δ=1.90(3H); 2.90(6H); 3.40-4.40(4H); 5.05(2H) 5.20(1H); 5.50-6.10(2H) and 6.65-7.15(4H).

(C)

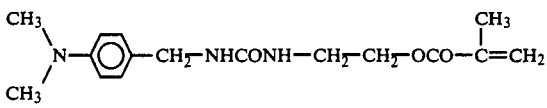

$^1$H-NMR: δ=1.92(3H), 2.85(6H); 3.10-4.20(6H); 5.40-5.70(2H); 5.40-6.10(2H) and 6.5-7.15(4H).

(D)

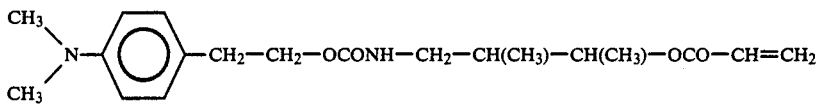

$^1$HNMR: δ=0.80-1.35(6H); 1.55-2.10(1H); 2.70-3.30(4H) 2.85(6H), 4.10-4.40(2H); 4.70-5.20(2H); 5.60-6.30(3H) and 6.60-7.25(4H).

(E)

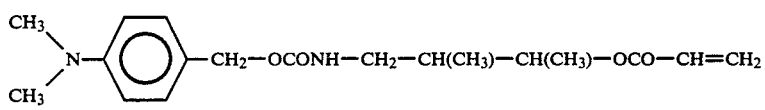

$^1$H-NMR: δ=0.80-1.35(6H); 1.50-2.05(1H); 2.85(6H) 3.05-3.25(2H); 4.70-5.25(2H); 4.90(2H); 5.60-6.30(3H) and 6.60-7.30(4H).

(F)

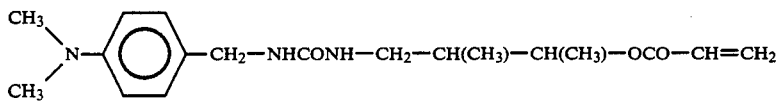

$^1$H-NMR: δ=0.75-1.25(6H); 1.45-2.00(1H); 2.5-3.15(2H); 2.85(6H); 4.00-4.20(2H); 4.65-5.10(1H); 5.60-6.60(5H) and 6.55-7.05(4H)

EXAMPLE 2

In each case 0.0025 mole of benzoyl peroxide or 0.0025 mole of amine is dissolved in 100 g of a mixture of 70 parts weight of bis-GMA and 30 parts by weight of triethylene glycol dimethacrylate. In each case 2 ml of peroxide solution and amine solution are mixed with one another.

The temperature during hardening is measured and the hardening time (time until the maximum temperature is reached) is determined.

| Amine | Hardening time |
|---|---|
| | 3 minutes 30 seconds |
| HOCH$_2$—CH$_2$—C$_6$H$_4$—N(CH$_3$)$_2$ (comparison experiment) A | 2 minutes 30 seconds |

-continued

| Amine | Hardening time |
|---|---|
| D | 2 minutes |

EXAMPLE 3

0.04% of ionol and 2.6% of $^R$Tinuvin P are dissolved in a mixture of 62 parts by weight of bis-GMA and 38 parts by weight of triethylene glycol dimethacrylate.

In each case 0.007 mole of the amine D or of the comparison experiment from Example 2 is dissolved in 100 g of this solution. In each case 10 g of silanized glass ceramic are processed to pastes with in each case 4 g of these solutions.

0.04% of ionol is dissolved in a mixture of 62 parts by weight of bis-GMA and 38 parts by weight of triethylene glycol dimethacrylate.

0.007 mole of benzoyl peroxide is dissolved in 100 g of this solution and the solution is processed to a paste in the same way as the amine solutions. If equal parts in the amine paste containing the amine of the comparison experiment and the peroxide paste are mixed, the mixture hardens in 3 minutes and 10 seconds. If equal parts of the amine paste containing amine D and the peroxide paste are mixed, the mixture hardens in 1 minute 30 seconds.

It will be understood that the specification and examples are illustrative but not limitative of the present invention and that other embodiments within the spirit and scope of the invention will suggest themselves to those skilled in the art.

We claim:

1. A compound of the formula

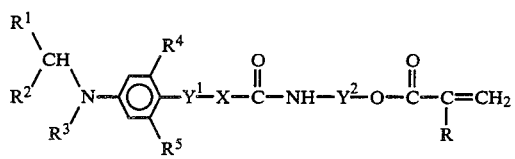

in which
R represents hydrogen or a methyl group,
$Y^1$ represents an optionally branched alkylene radical with 1 to 6 C atoms,
$Y^2$ represents an optionally branched alkylene radical with 2 to 8 C atoms,
X denotes oxygen or an —NH— group,
$R^1$ and $R^2$ are identical or different and denote hydrogen, or an alkyl, alkenyl, cycloalkyl, cycloalkenyl, aryl, aralkyl or alkylaryl group which has up to 11 C atoms and is optionally substituted by one or more,
hydroxyl or amino, groups, or
$R^1$ and $R^2$ together form a 3-membered to 6-membered ring, which optionally contains nitrogen, oxygen or sulphur as hetero-atoms,
$R^3$ has the meaning of $R^1$ or represents a group

or
$R^2$ and $R^3$, together with the

group, form a 5-membered or 6-membered ring, which optionally contains oxygen as a further heteroatom, and
$R^4$ and $R^5$ are identical or different and represent hydrogen, an alkyl or alkenyl group which has up to 10 C atoms and is optionally substituted by halogen, or halogen.

2. A compound according to claim 1, in which $R^1$ is hydrogen.

3. A compound according to claim 1, in which $R^2$ is hydrogen or methyl.

4. A compound according to claim 1, in which $R^3$ is methyl or ethyl.

5. A compound according to claim 1, in which $R^4$ and $R^5$ each independently is hydrogen or methyl.

6. A compound according to claim 5, in which both $R^4$ and $R^5$ are hydrogen.

7. A compound according to claim 1, wherein such compound is

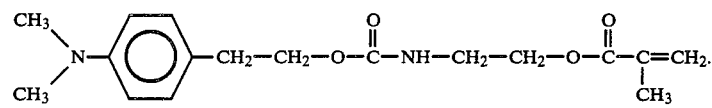

8. A compound according to claim 1, wherein such compound is

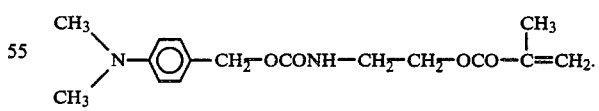

9. A compound according to claim 1, wherein such compound is

10. A compound according to claim 1, wherein such compound is

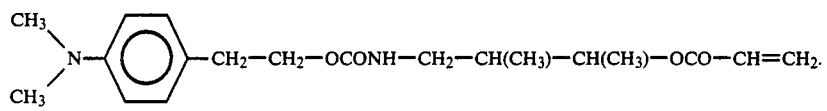
11. A compound according to claim 1, wherein such compound is
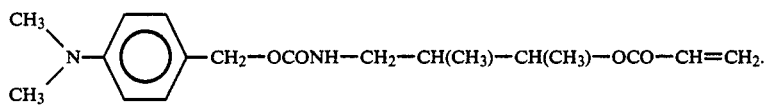
12. A compound according to claim 1, wherein such compound is
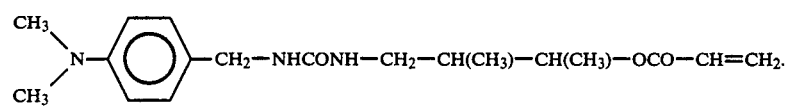
* * * * *